(12) United States Patent
Juretich et al.

(10) Patent No.: US 8,459,968 B2
(45) Date of Patent: Jun. 11, 2013

(54) PERISTALTIC PUMP CASSETTE AND METHOD OF INSTALLING SAME

(75) Inventors: Jeffery T. Juretich, Herriman, UT (US); Ramji L. Gupta, Williamsville, NY (US); David A. Ross, Columbiaville, MI (US); Kent F. Beck, Layton, UT (US); Matthew L. Alesse, West Seneca, NY (US)

(73) Assignee: Curlin Medical Inc., East Aurora, NY (US)

( * ) Notice: Subject to any disclaimer, the term of this patent is extended or adjusted under 35 U.S.C. 154(b) by 143 days.

(21) Appl. No.: 13/236,237

(22) Filed: Sep. 19, 2011

(65) Prior Publication Data
US 2013/0071272 A1  Mar. 21, 2013

(51) Int. Cl.
*F04B 43/12* (2006.01)
(52) U.S. Cl.
USPC .................................. 417/477.2; 417/477.9
(58) Field of Classification Search
USPC . 417/477.1, 477.2, 474, 477.9, 360; 604/153; 403/353, 361
See application file for complete search history.

(56) References Cited

U.S. PATENT DOCUMENTS

| | | | | |
|---|---|---|---|---|
| 3,723,030 A * | 3/1973 | Gelfand | | 417/475 |
| 3,927,955 A * | 12/1975 | Spinosa et al. | | 417/477.3 |
| 4,009,507 A * | 3/1977 | Lascarrou | | 16/265 |
| 4,673,334 A * | 6/1987 | Allington et al. | | 417/53 |
| 4,735,558 A * | 4/1988 | Kienholz et al. | | 417/477.2 |
| 4,886,431 A * | 12/1989 | Soderquist et al. | | 417/477.2 |
| 4,925,376 A * | 5/1990 | Kahler | | 417/477.11 |
| 5,211,548 A * | 5/1993 | Okada | | 417/474 |
| 5,213,483 A * | 5/1993 | Flaherty et al. | | 417/477.2 |
| 5,257,917 A * | 11/1993 | Minarik et al. | | 417/475 |
| 5,388,972 A * | 2/1995 | Calhoun et al. | | 417/477.11 |
| 5,397,222 A * | 3/1995 | Moss et al. | | 417/477.2 |
| 5,518,378 A * | 5/1996 | Neftel et al. | | 417/477.2 |
| 5,601,420 A * | 2/1997 | Warner et al. | | 417/474 |
| 5,709,539 A * | 1/1998 | Hammer et al. | | 417/477.3 |
| 5,752,813 A * | 5/1998 | Tyner et al. | | 417/477.2 |
| 5,788,671 A * | 8/1998 | Johnson | | 604/131 |
| 5,927,956 A * | 7/1999 | Lim et al. | | 417/477.13 |
| 7,214,038 B2 * | 5/2007 | Saxer et al. | | 417/477.2 |
| 7,223,079 B2 * | 5/2007 | Ortega et al. | | 417/53 |
| 7,287,968 B2 * | 10/2007 | Haser et al. | | 417/477.9 |
| 7,467,932 B2 * | 12/2008 | Schann et al. | | 417/477.1 |
| 7,722,338 B2 * | 5/2010 | Nordell et al. | | 417/477.11 |
| 7,934,912 B2 | 5/2011 | Voltenburg et al. | | |
| 2007/0212240 A1 * | 9/2007 | Voyeux et al. | | 417/477.2 |
| 2009/0053085 A1 * | 2/2009 | Thompson et al. | | 417/477.2 |

(Continued)

*Primary Examiner* — Charles Freay
*Assistant Examiner* — Alexander Comley
(74) *Attorney, Agent, or Firm* — Hodgson Russ LLP

(57) ABSTRACT

A peristaltic pump assembly comprises a pump and a removable cassette. The pump includes a pumping mechanism portion having opposed inner and outer walls defining a slot opening therebetween, and further having a cassette mounting pin extending at least partially across the slot opening. The removable cassette includes a cylindrical hinge journal and a mounting channel merging in a radial direction with the hinge journal, whereby the cassette is mounted on the mounting pin by inserting the removable cassette into the slot opening between the inner and outer walls of the pumping mechanism portion in a radial direction of the mounting pin such that the mounting pin is passed through the mounting channel and received by the hinge journal. The mounting pin and hinge journal are configured to allow the removable cassette to rotate about the mounting pin into and out of an installed position.

20 Claims, 11 Drawing Sheets

U.S. PATENT DOCUMENTS

2009/0087325 A1    4/2009  Voltenburg, Jr. et al.
2009/0087326 A1*   4/2009  Voltenburg et al. ........ 417/477.2
2009/0087327 A1*   4/2009  Voltenburg et al. ........ 417/477.2
2010/0226716 A1*   9/2010  Imai .............................. 403/361

* cited by examiner

PERISTALTIC PUMP CASSETTE AND METHOD OF INSTALLING SAME

FIELD OF THE INVENTION

The present disclosure relates generally to peristaltic pump assemblies and removable cassettes therefore.

BACKGROUND OF THE INVENTION

Rotary-style peristaltic pumps often generally include a cassette mounted to and supported by a pump body. In some instances, the pump body includes a cavity formed therein and configured to receive a planetary assembly of rollers. The rollers revolve together when rotationally driven by a drive shaft when the drive shaft is powered by a pump motor.

The cassette generally includes a body having a flexible tube disposed therethrough. When the cassette is mounted to the pump body, the flexible tube surrounds a portion of the assembly of rollers. In response to rotational movement of the rollers, portions of the flexible tube in contact with the rollers compress or otherwise occlude against a wall of the cassette. As a result, fluid traveling through the tube is temporarily trapped in the tube between the occluded points. The trapped fluid is released from the tube when the occlusion force on the tube is released. In this manner, fluid is urged through the tube via peristaltic wave action.

Peristaltic infusion pumps are often used to deliver fluid in a controlled manner, such as, for example, the intravenous delivery of pharmaceutical compositions to a patient. These peristaltic pumps typically use disposable cassettes, where the pump assembly is designed to accommodate the loading of the cassette, as well as the removal of the cassette from the assembly. Such designs, however, may undesirably involve relatively difficult cassette loading and removal schemes.

U.S. Pat. No. 7,934,912 discloses a peristaltic pump assembly wherein a removable cassette is installed in the pump body by sliding the cassette onto a cylindrical mounting pin extending from the pump body. The cassette includes a hinge journal sized to receive the mounting pin, and the cassette is slid onto the mounting pin in an axial direction of the mounting pin. Once installed in this manner, the cassette is rotatable about the mounting pin until a retaining feature on the cassette spaced from the hinge journal engages a corresponding retaining feature on the pump body. Thus, if the axis of the mounting pin is considered the Z axis, the cassette must be moved along the Z axis toward the pump body to slide the cassette on the mounting pin, and then the cassette may be rotated about the Z-axis in an X-Y plane. Similar but reverse steps are necessary to remove the cassette from the pump body. While this "side loading" arrangement provides for easy installation and removal of the cassette, the cassette mounting pin must be exposed or accessible to receive the cassette and allow removal of the cassette. A portion of the cassette that includes the hinge journal must also remain exposed or accessible for the same reasons. Therefore, improved protection against inadvertent movement of the cassette is desired.

SUMMARY OF THE INVENTION

The present invention is embodied by a removable cassette and a peristaltic pump assembly designed such that the cassette may be installed into and removed from a pumping mechanism portion of the pump in a radial direction of a cassette mounting pin extending at least partially across a fixed slot in which the pumping mechanism portion is situated. In this manner, the invention avoids the use of a door or cover that opens to expose the pumping mechanism portion. The invention is further embodied by a method of installing a removable cassette on a peristaltic pump and a method of removing a cassette from a peristaltic pump.

A removable cassette formed in accordance with an embodiment of the present invention generally comprises a cassette body including rear wall, a front wall, a perimeter wall connecting the rear and front walls, and a hinge journal formed therein through the rear wall for slidably receiving the mounting pin of the peristaltic pump, wherein the cassette body is rotatable about an axis of the mounting pin relative to the pump body. The cassette body further including a mounting channel through the rear wall and the perimeter wall. The mounting channel communicates with the hinge journal, whereby the mounting pin is received into the hinge journal via the mounting channel by moving the cassette body in a radial direction relative to the mounting pin.

A peristaltic pump assembly embodying the present invention may comprise a removable cassette as summarized in the preceding paragraph in combination with a peristaltic pump that includes a pumping mechanism portion having an inner wall and an outer wall opposing each other to define a slot opening therebetween, the pumping mechanism portion further having a cassette mounting pin extending at least partially across the slot opening. The mounting pin may be supported on a spring biased swing arm of the pumping mechanism portion. The removable cassette is mounted on the mounting pin by inserting the cassette into the slot opening between the inner and outer walls of the pumping mechanism portion in a radial direction of the mounting pin such that the mounting pin is passed through the mounting channel of the cassette and received by the hinge journal of the cassette. The mounting pin and hinge journal are configured to allow the removable cassette to rotate about the mounting pin into and out of a fully installed position.

In another embodiment, the invention provides a method of installing a removable cassette on a peristaltic pump including a generally cylindrical mounting pin. The installation method comprises the steps of aligning the cassette relative to the mounting pin such that a mouth of a mounting channel of the cassette is radially adjacent the mounting pin, moving the cassette in a radial direction relative to the mounting pin such that the mounting pin passes through the mounting channel and into a hinge journal of the cassette, and rotating the cassette about the mounting pin into an installed position.

In a further embodiment, the invention provides a method of removing a cassette from a peristaltic pump including a generally cylindrical mounting pin received by a cylindrical hinge journal of the cassette. The removal method generally comprises the steps of rotating the cassette about the mounting pin until a truncated circumferential portion of the mounting pin is aligned with a juncture between the hinge journal and a mounting channel of the cassette, and moving the cassette in a radial direction relative to the mounting pin such that the mounting pin passes from the hinge journal into the mounting channel and out of the cassette via the mounting channel.

BRIEF DESCRIPTION OF THE DRAWING VIEWS

Features and advantages of embodiment(s) of the present disclosure will become apparent by reference to the following detailed description and drawings, in which like reference numerals correspond to similar, though perhaps not identical components. Reference numerals having a previously described function may or may not be described in connection with other drawings in which they appear.

DETAILED DESCRIPTION OF THE INVENTION

Embodiments of the peristaltic pump assembly and removable cassette disclosed herein advantageously provide a simplified pump assembly design to facilitate loading and removal of a cassette to and from a pump body, and yet protect against inadvertent movement of the cassette. The mounting and removal processes are relatively simple and efficient, thereby eliminating the need for extensive operator training. The cassette mounting process reduces or substantially eliminates errors with respect to improper positioning of the cassette when assembled with the pump body, and audible and tactile feedback assure the user that the cassette is mounted properly in the pump assembly. As a further advantage, the pump assembly does not require the use of a door, which has a tendency to wear down and/or break from continuous use.

Figure 4:
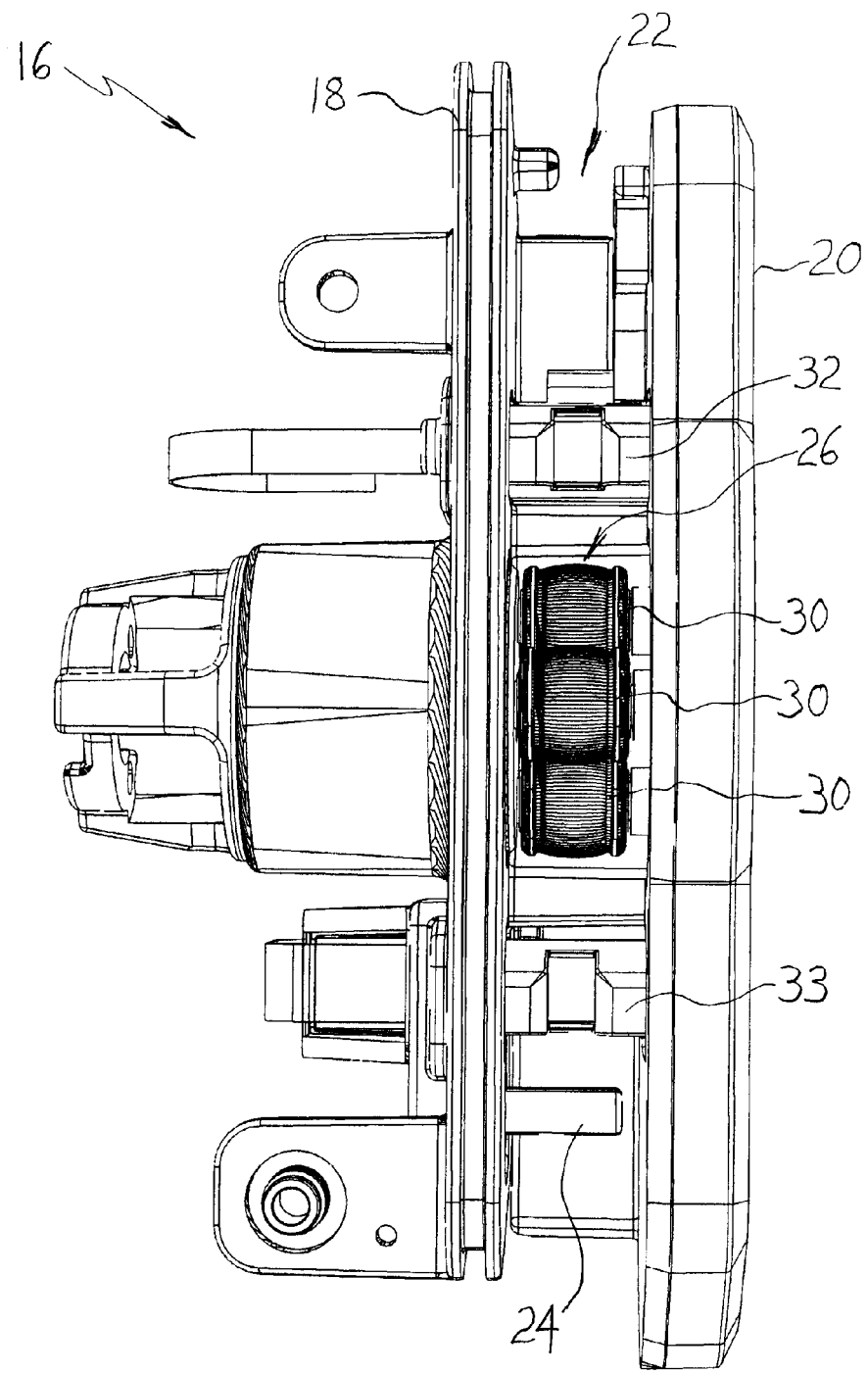
FIG. 4 is an enlarged view of a pumping mechanism portion of the peristaltic pump shown in FIG. 3, looking directly into a slot opening defined by an inner wall and an outer wall of the pumping mechanism portion.

Reference is initially made to FIGS. 1-5 of the drawings. A peristaltic pump assembly 10 generally comprises a peristaltic pump 12 and a removable cassette 50, wherein cassette 50 is depicted in an installed position in pump 12 in FIGS. 1 and 5 and in a partially installed position in pump 12 in FIG. 2. Peristaltic pump 12, shown without cassette 50 in FIG. 3, includes a pump body 14 and a pumping mechanism portion 16 coupled to pump body 14. Pumping mechanism portion 16 may have an inner wall 18 and an outer wall 20 opposing each other to define a slot opening 22 therebetween. Pumping mechanism portion 16 includes a cassette mounting pin 24 extending at least partially across slot opening 22, as best seen in FIG. 4.

Pumping mechanism portion 16 also includes a roller assembly 26 driven by a pump motor (not shown) to rotate about an axis 27 defined by a drive shaft 28 extending through a bore in inner wall 18. Roller assembly 26 has a plurality satellite pinch rollers 30 angularly spaced about axis 27, each pinch roller 30 being mounted to freely rotate about a respective pin 31 extending parallel to drive shaft 28. A shelf 25 is fixed relative to inner wall 18 and includes an arc-shaped recess 29 adjacent roller assembly 26 to accommodate rotation of the roller assembly.

Pumping mechanism portion 16 may further include an upstream sensor 32 and a downstream sensor 33 substantially aligned with one another and arranged such that roller assembly 26 is between sensors 32 and 33. In a current advantageous configuration best seen in FIG. 5, downstream sensor 33 and mounting pin 24 are supported at a distal end of a swing arm 34 adjacent one another. A proximal end of swing arm 34 is pivotally mounted to inner wall 18 by a pivot pin 35, and a spring 39 is arranged to act between shelf 25 and swing arm 34 to bias swing arm 34 in a counter-clockwise direction about an axis of pivot pin 35, wherein the pivot pin axis is parallel to rotational axis 27 of roller assembly 26. By this configuration, mounting pin 24 is resiliently biased such that when cassette 50 is installed on the mounting pin, the cassette is resiliently biased toward contact with the roller assembly and downstream sensor is maintained at a constant position relative to the cassette.

By way of example, upstream sensor 32 may be a pressure sensor designed to detect a pressure increase within tubing of an installed cassette 50 indicative of a possible occlusion or flow blockage. By way of further example, downstream sensor 33 may be a pressure sensor for detecting occlusions and/or an air-in-line sensor for detecting air bubbles in fluid being pumped through tubing of cassette 50. It is to be understood that the pressure sensor(s) 32, 33 may be any suitable pressure sensors, e.g., piezoelectric pressure sensors; and that the air-in-line sensors 33 may be any suitable sensors, e.g., ultrasonic air-in-line sensors. The sensors 32 and 33 are also generally shaped to complement the shape of the cassette 50. Further, the sensors 32 and 33, in combination with the opposed walls 18 and 20, are also generally configured to guide cassette 50 and tubing thereof as the cassette is rotated into its installed position as described below.

Pump body 14 includes a display 36 that corresponds with a keypad 38 for inputting user information such as, for example, patient identification number, drug identification number, operator identification number, or the like. The display 36 also provides visual feedback to the operator or user of the pump assembly 10 regarding, for example, the amount of medication administered to a patient, the flow rate of the medication, and the time for medication administration.

Figure 6:
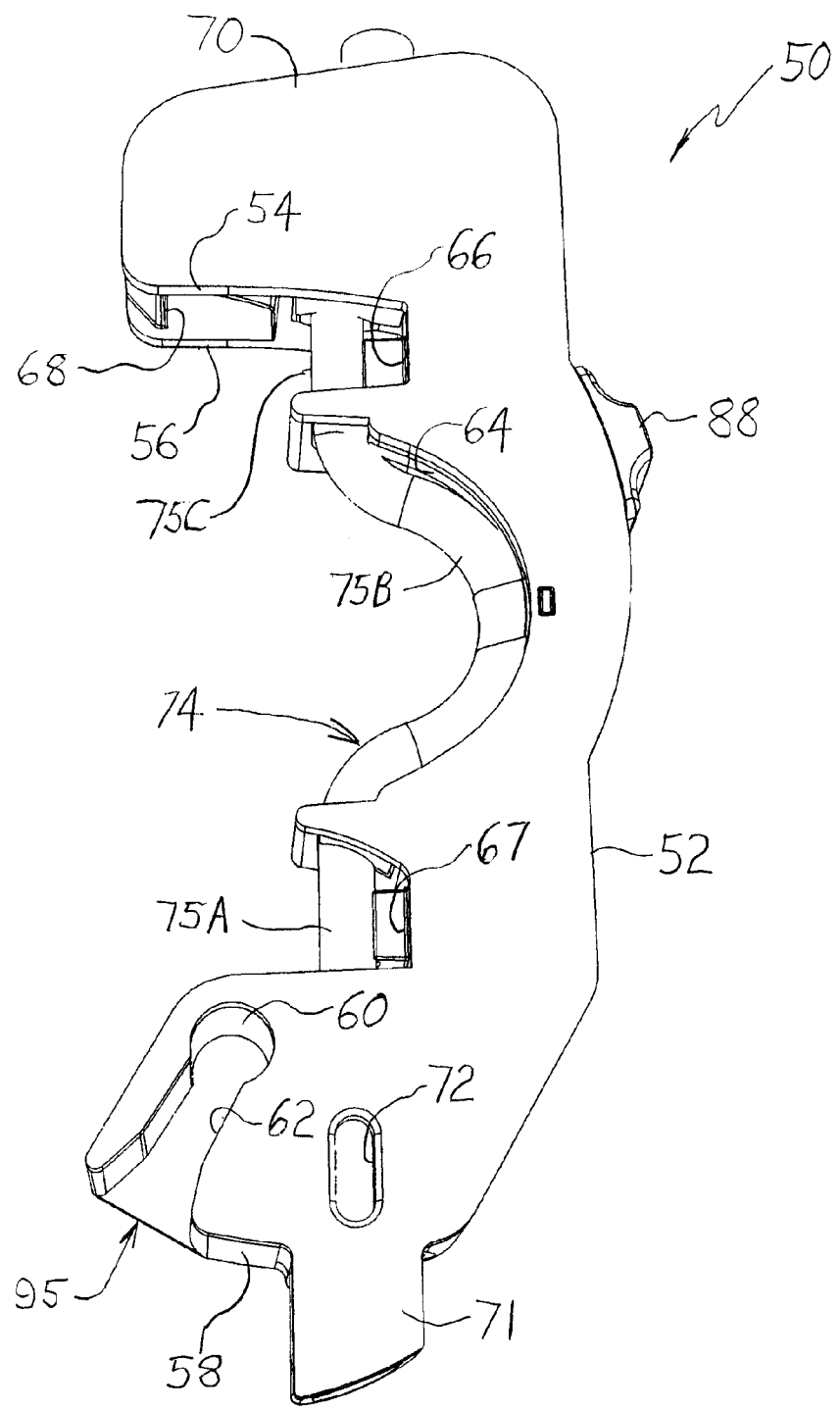
FIG. 6 is a rear perspective view of the removable cassette shown for illustrating a mounting channel and other features of the cassette.

Referring also now to FIG. 6, cassette 50 comprises a cassette body 52 including a rear wall 54, a front wall 56, a perimeter wall 58 connecting the rear and front walls, and a cylindrical hinge journal 60 formed therein through rear wall 54 for slidably receiving mounting pin 24 of the peristaltic pump such that cassette body 52 is rotatable about an axis of mounting pin 24 relative to pump body 14. The cassette body 52 further includes a mounting channel 62 through rear wall 54 and perimeter wall 58. As may be seen in FIG. 6, mounting channel 62 communicates with hinge journal 60. Cassette body 52 also defines a concave race surface 64, which may be arc shaped as illustrated in FIG. 6. Cassette body 52 may be provided with an upstream recess 66 and a downstream recess 67 configured for respectively receiving upstream sensor 32 and downstream sensor 33 when cassette 50 is rotated into its installed position. In the embodiment shown, cassette body 52 includes a closure catch surface 68 arranged in perimeter wall 58 near an upstream end 70 of the cassette body, and a view window 72 through rear wall 54 and front wall 56 near a downstream end 71 of the cassette body.

Figure 7:
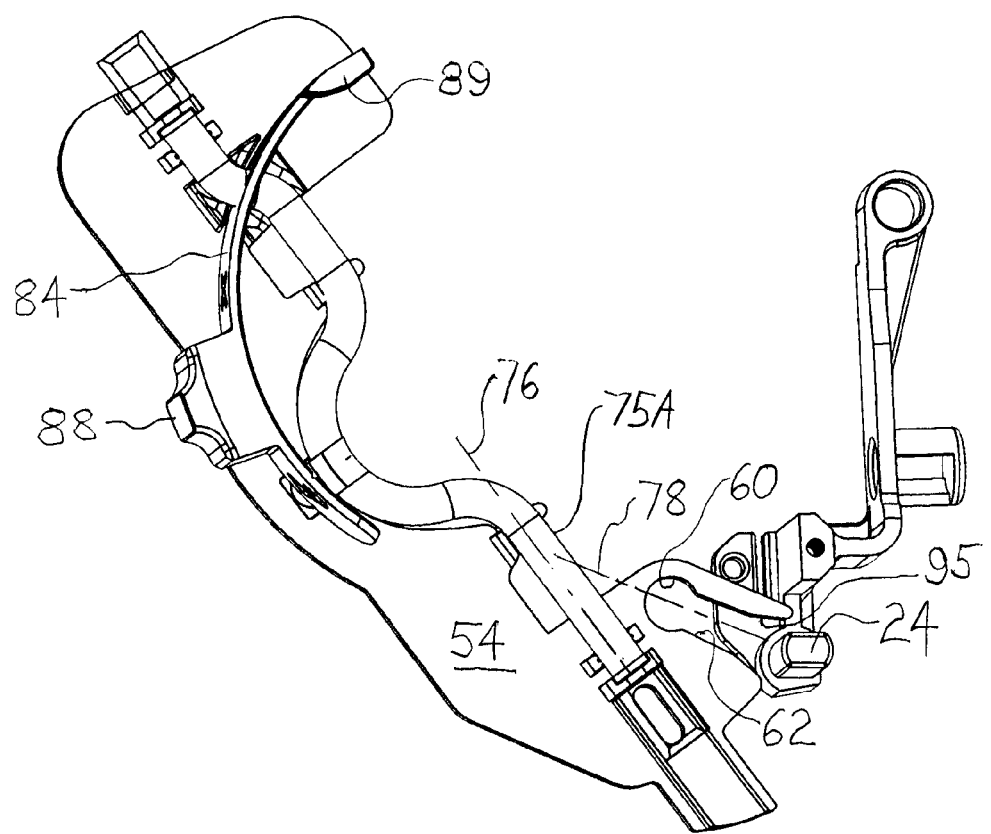
FIG. 7 is a front perspective view of the cassette and a swing arm of the pumping mechanism portion of the peristaltic pump, wherein a front wall of the cassette is omitted to show the mounting channel in relation to a mounting pin carried by the swing arm, and wherein the cassette is shown in an uninstalled position.
Figure 8:
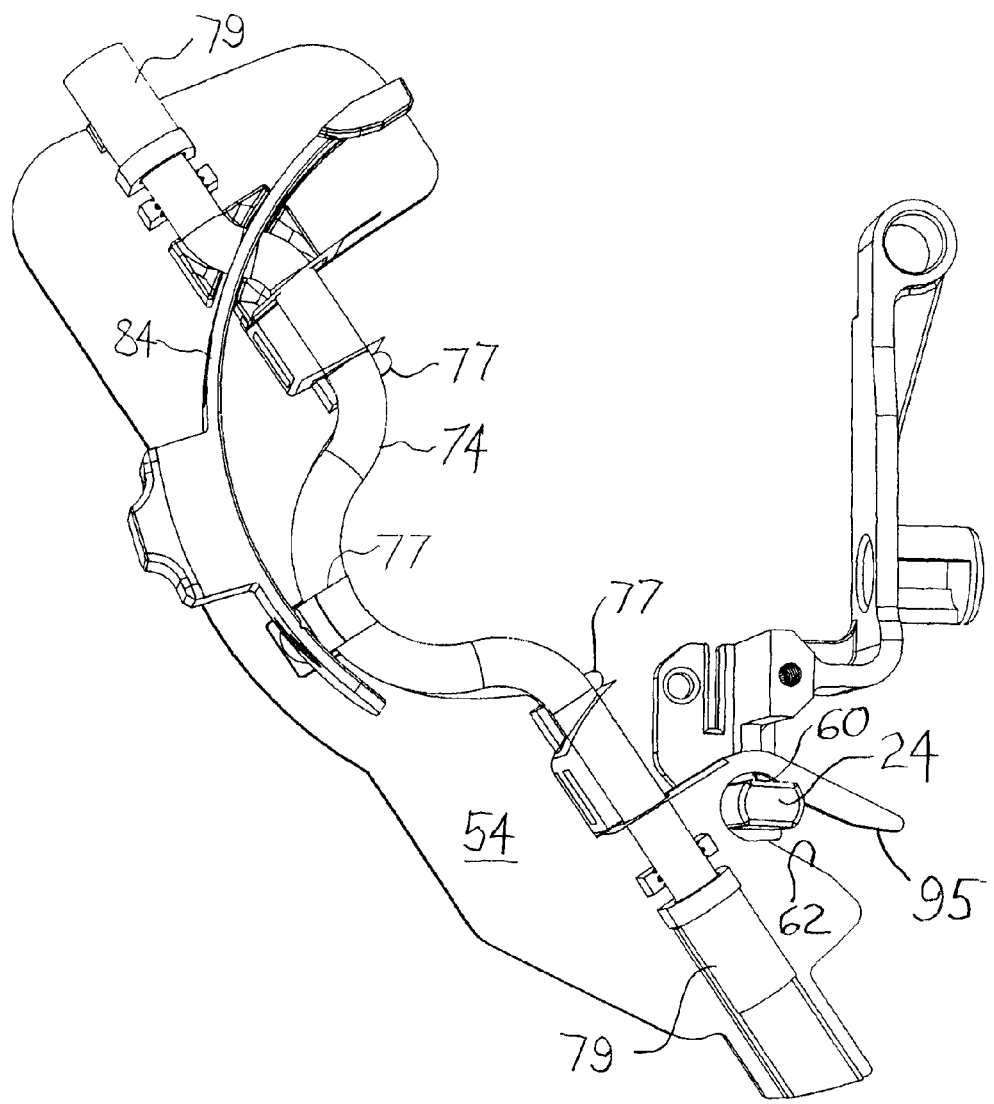
FIG. 8 is a view similar to that of FIG. 7, however the cassette is shown in a partially installed position.
Figure 9:
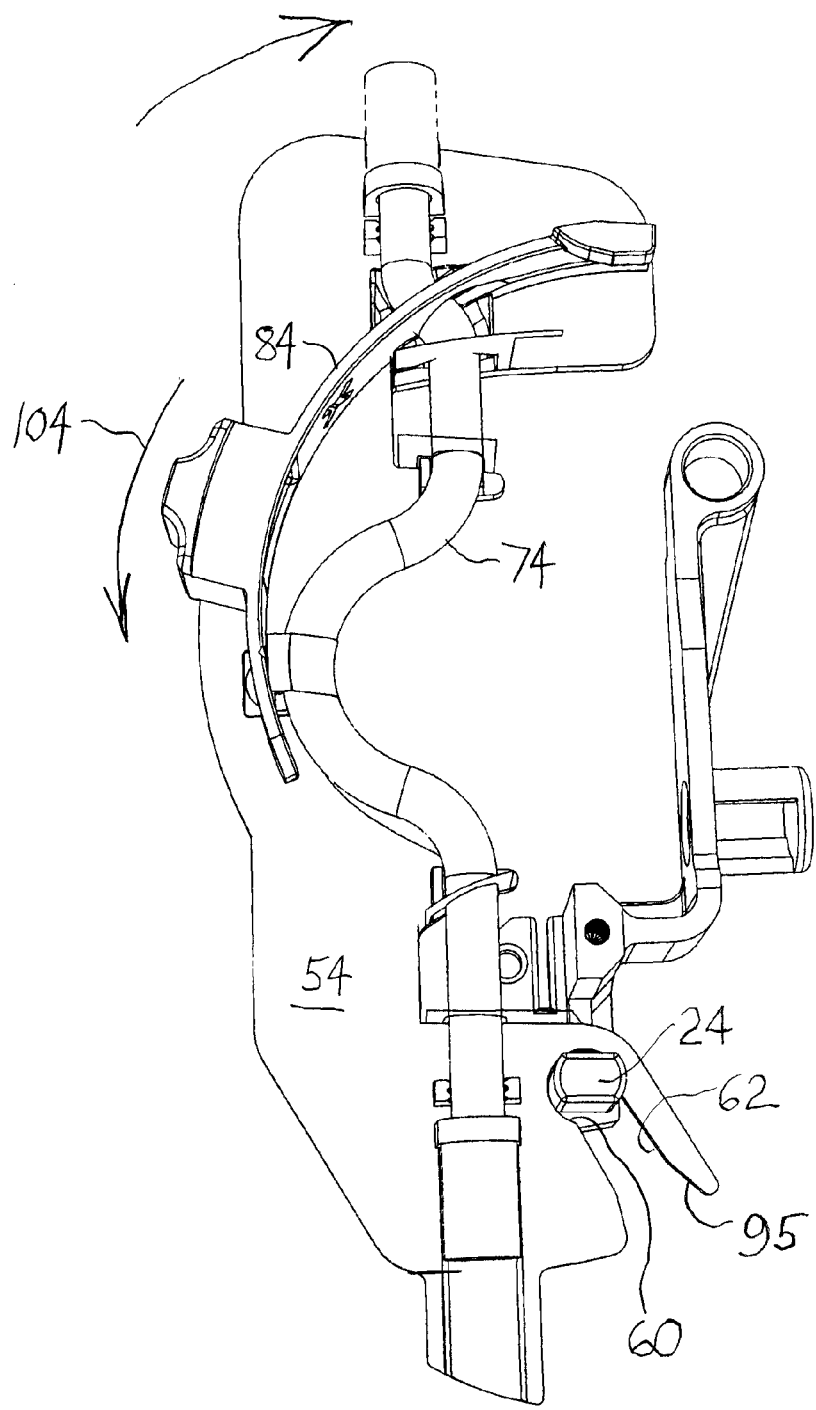
FIG. 9 is a view similar to that of FIG. 7, however the cassette is shown in a fully installed position.

Cassette 50 further comprises a segment of compressible tubing 74, also depicted in FIGS. 7-9, extending through the cassette body from upstream end 70 to downstream end 71. Tubing segment 74 may include an outlet portion 75A near downstream end 71 that extends in a first direction 76, and mounting channel 62 may be an elongated channel extending in a second direction 78 inclined relative to the first direction 76 followed by outlet portion 75A of tubing segment 74. Tubing segment 74 also includes an inlet portion 75C near upstream end 70 of cassette body 52 and a middle portion 75B located between first and second portions 75A and 75C. Tubing segment 74 may be held in place by tubing guides 77 fixed to or integrally formed with cassette body 52. The outlet and inlet portions 75A and 75C may be provided with tubing connectors 79 for coupling downstream supply tubing 80 and upstream supply tubing 82 to the outlet and inlet tubing portions, respectively. As will be understood, downstream supply tubing 80 carries infusion liquid (e.g., medication) from cassette 50 to the patient, and upstream supply tubing 82 carries infusion liquid from a source container (not shown) to the cassette. The middle portion 75B of tubing segment 74 is intended to be engaged on one side by pinch rollers 30, and on an opposite side by race surface 64. Tubing segment 74 may be made of a polymeric material, non-limiting examples of which include silicones, AUTOPRENE (an opaque thermoplastic rubber with high wear resistance derived from SANTOPRENE, commercially available from Advanced Elastomer Systems, a subsidiary of ExxonMobil Chemical located in Houston, Tex.), VITON (a black fluoroelastomer with resistance to concentrated acids, solvents, ozone, radiation and temperatures up to 200° C. with good chemical compatibility, commercially available from DuPont Performance Elastomers located in Wilmington, Del.), TYGON (good chemical resistance with a clear finish, commercially available from Saint-Gobain Performance Plastics Corporation located in Akron, Ohio), PROTHANE II (a transparent, blue, polyester, polyurethane tubing with good chemical resistance, commercially available from Randolph Austin Company located in Manchaca, Tex.), and/or the like, and/or combinations thereof. The inner diameter of the tubing segment 74 may be selected based on the desirable flow rates and the desirable viscosities of the fluid that will flow therethrough. When cassette 50 is in the installed position, tubing segment 74 surrounds a portion of roller assembly 26.

Figure 5:
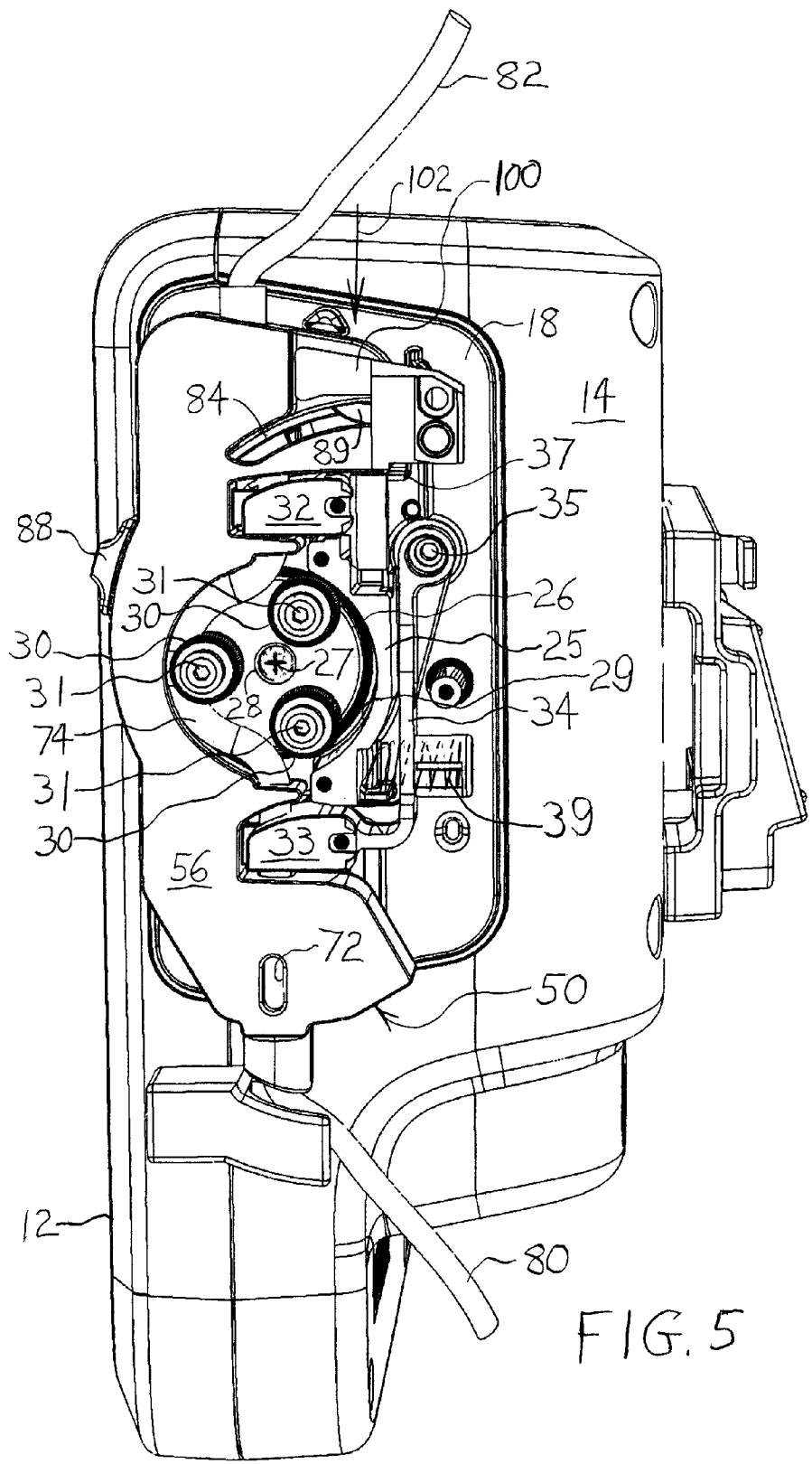
FIG. 5 is a view of the peristaltic pump assembly, wherein the outer wall of the pumping mechanism portion is omitted to show the removable cassette in the installed position.

As best understood with reference to FIG. 5, when pump 12 is operating, rotational movement of roller assembly 26 causes pinch rollers 30 to sequentially compress tubing segment 74 to peristaltically pump fluid through the tubing segment to create a pressurized flow thereof. Tubing segment 74 compresses or otherwise occludes at a number of points in contact with the rollers 30 and race surface 64 on the other side thereof when roller assembly 26 and individual rollers 30 are rotating. Fluid is trapped in tubing segment 74 between two points of occlusion (i.e., from one roller 30 to an adjacent roller 30) and urged forward. Thus, fluid is passed or moved through tubing segment 74 at a flow rate proportional to the rotational rate (rpm) of drive shaft 28 via peristaltic wave action.

Figure 11:
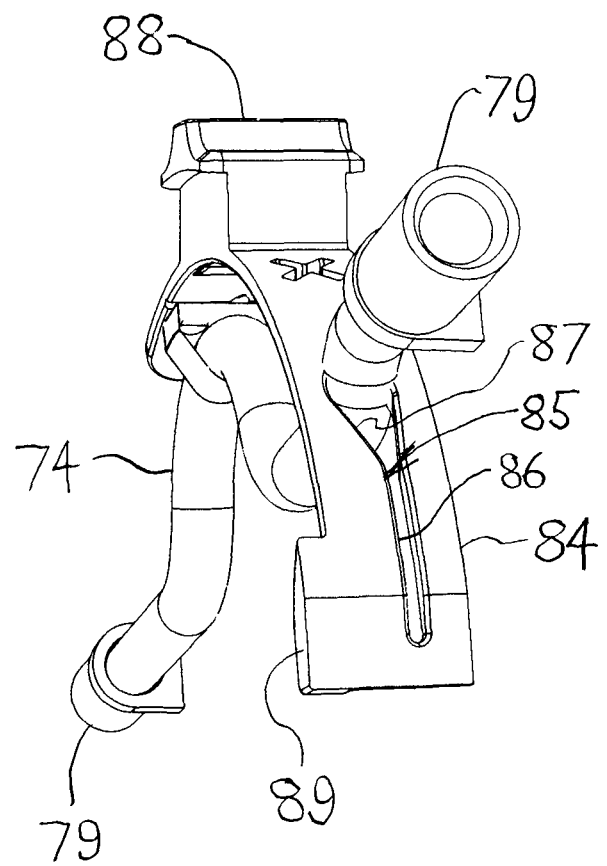
FIG. 11 is a view showing a slidable pinch occluder of the cassette.

Cassette 50 also comprises an arc-shaped pinch occluder 84 slidably mounted on cassette body 52 and operable to selectively open and close compressible tubing 64 to control liquid flow through the tubing. FIG. 11 provides another view of pinch occluder 84. In the embodiment shown and described herein, pinch occluder 84 includes a shaped passage 85 having a narrow region 86 for pinching tubing segment 74 to shut off flow and a wide region 87 that does not pinch tubing segment 74 and thus allows flow through the tubing segment. Pinch occluder 84 also includes a slider button 88 allowing a user to manually slide the pinch occluder along an arcuate path relative to cassette body 52 and tubing segment 74 between a non-occluding position as shown in FIG. 11, wherein tubing segment passes through wide region 87, and an occluding position (not shown), wherein tubing segment 74 passes through narrow region 86 and is pinched closed. Pinch occluder may further include an enlarged end portion 89 for preventing unintended cassette ejection as described below.

Figure 10:
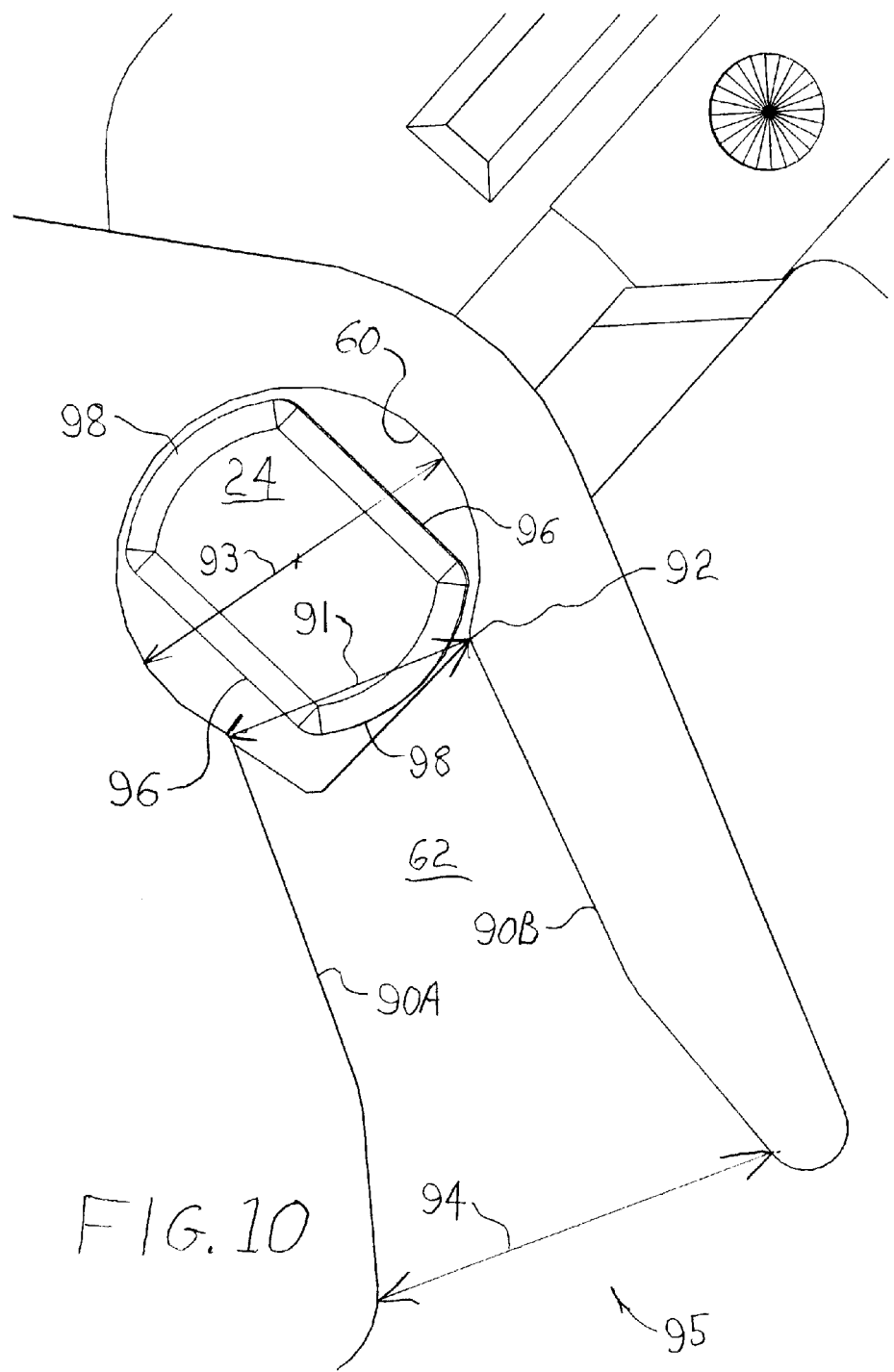
FIG. 10 is an enlarged view of the mounting channel and mounting pin corresponding to a partially installed position of the cassette for illustrating geometric features of the mounting channel and mounting pin.

Reference is again made to FIG. 6, and also to FIG. 10. Mounting channel 62 includes a pair of opposed channel walls 90A, 90B. In accordance with a currently preferred embodiment, a spacing 91 between the pair of channel walls 90A, 90B at a juncture 92 of mounting channel 62 with hinge journal 60 is less than an inner diameter 93 of the hinge journal. Also in accordance with a currently preferred embodiment, a spacing 94 between the pair of channel walls 90A, 90B at a location 95 where the mounting channel 62 opens through perimeter wall 58 (i.e., at the mouth of channel 62) is greater than the inner diameter 93 of hinge journal 60. The pair of channel walls 90A, 90B may converge linearly from the location 95 where mounting channel 62 opens through the perimeter wall 58 to the juncture 92 of mounting channel 62 with hinge journal 60. As shown in FIG. 6, mounting channel 62 may be covered by the front wall 56 of cassette body 52.

Mounting pin 24 and hinge journal 60 are configured to allow the removable cassette 50 to rotate about the mounting pin into and out of an installed position. Mounting pin 24 may be generally cylindrical in shape and have a diameter chosen to fit within hinge journal 60 to provide rotational stability. A circumference of mounting pin 24 may be truncated to enable the mounting pin to pass through mounting channel 62 and into hinge journal 60, as will be described in greater detail below. In the embodiment depicted herein, the circumference of mounting pin 24 is truncated by providing a pair of flats 96 diametrically opposite one another. As will be understood, the circumference of mounting pin 24 may be truncated by other configurations. By way of non-limiting example, a single flat may be provided rather than a pair of flats, or a concave or even a convex truncation shape may be used. As will be understood, a portion or portions 98 of the original circumference of mounting pin 24 are maintained for rotational stability when the mounting pin is received by hinge journal 60. Mounting pin 24 may have a substantially stout configuration, and may be manufactured from metal, such as an aluminum alloy, steel alloy, or stainless steel alloy, or from hard plastic. As described earlier, mounting pin 24 may be carried on spring-biased swing arm 34 so as to resiliently bias an installed cassette 50, particularly tubing segment 74 of the cassette, toward contact with at least one of the pinch rollers 30 of roller assembly 26. In this way, even and consistent force is applied by pinch rollers 30 against tubing segment 74 in spite of small variations in the cassettes from one cassette to another.

Figure 1:
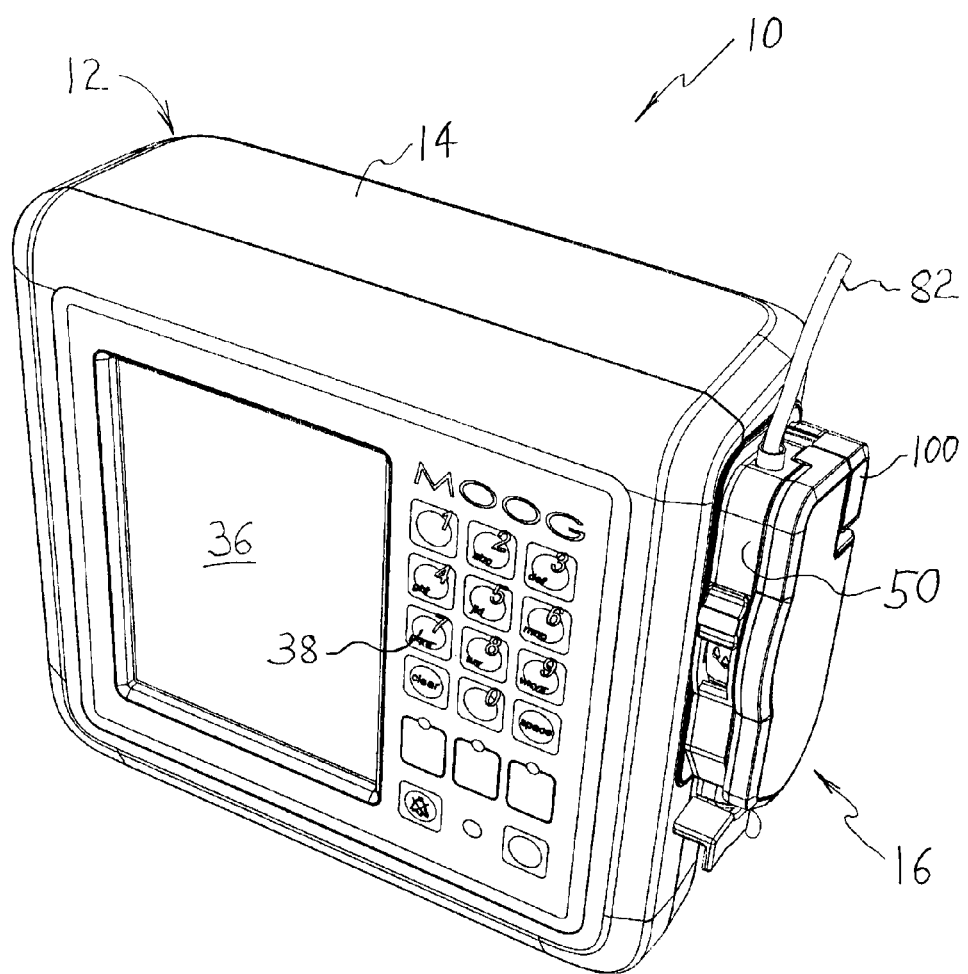
FIG. 1 is a perspective view of a peristaltic pump assembly including a removable cassette formed in accordance with an embodiment of the present invention, wherein the removable cassette is shown in an installed position.
Figure 2:
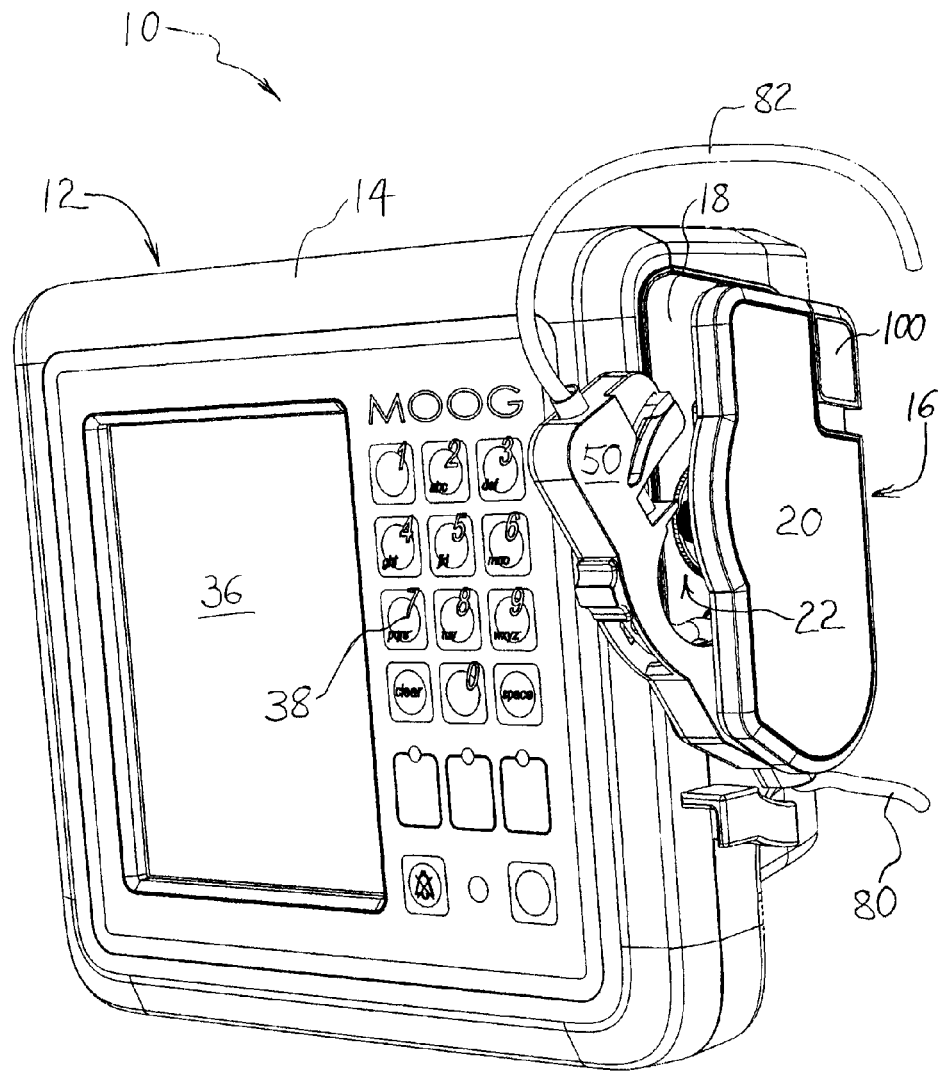
FIG. 2 is a perspective view of the peristaltic pump assembly of FIG. 1, wherein the removable cassette is shown in a partially installed position.
Figure 3:
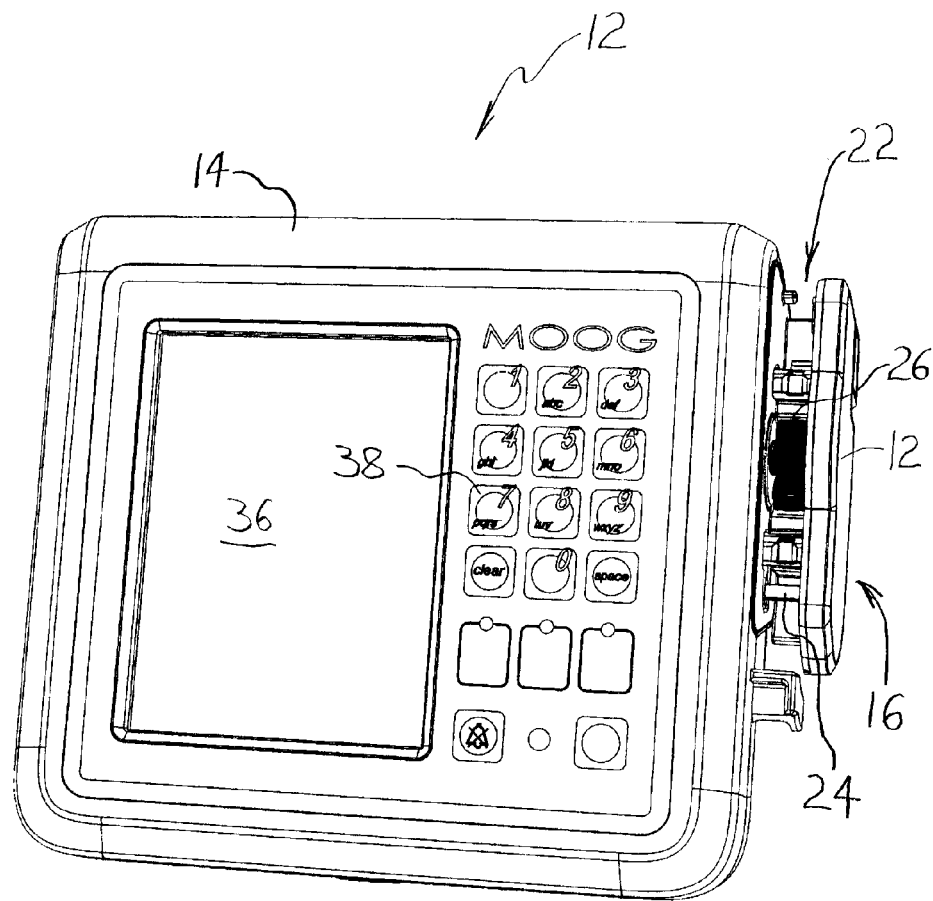
FIG. 3 is a perspective view of a peristaltic pump of the peristaltic pump assembly, without the removable cassette.

FIG. 2 shows cassette 50 mounted on mounting pin 24 but rotated out of the installed position. As may be seen in FIG. 6, closure catch surface 68 on cassette body 52 is arranged and configured for engagement by a resiliently deflectable retaining member 37 provided within slot opening 22 of pumping mechanism portion 16 when cassette 50 is rotated about mounting pin 24 into the installed position. When catch surface 68 and retaining member 37 are engaged with one another, rotation of cassette 50 about mounting pin 24 is prevented. An eject button 100 is operable in the direction of arrow 102 (shown in FIG. 5) to disengage retaining member 37 from catch surface 68 and thereby permit rotation of cassette 50 about mounting pin 24. As may be understood, eject button 100 is not operable when pinch occluder 84 is in its non-occluding position because enlarged end portion 89 prevents eject button 100 from being moved in the direction of arrow 102 to disengage retaining member 37 from latch 100. Thus, an unintended or mistaken attempt to eject cassette 50 while tubing segment 74 is not occluded will fail. Pinch occluder 84 must be slid in the direction of arrow 104 to its occluding position to permit operation of eject button 100.

In accordance with an embodiment of the present invention, a method of installing removable cassette 50 on peristaltic pump 12 comprises the following steps described with reference to FIGS. 7-9. A first step is aligning the cassette 50 relative to mounting pin 24 such that a mouth of mounting channel 62 is radially adjacent the mounting pin, as illustrated in FIG. 7. Another step is moving the cassette 50 in a radial direction relative to mounting pin 24 such that the mounting pin passes through mounting channel 62 and into hinge journal 60 of the cassette, as depicted in FIG. 8. As may be understood, the steps mentioned above are facilitated by the truncated circumference of mounting pin 24, whereby the mounting pin is sized to pass through mounting channel 62 when the angular orientation of cassette 50 relative to mounting pin 24 is such that the pair of flats 96 are parallel or nearly parallel to channel walls 90A, 90B. In other words, the distance from flat-to-flat through the center of mounting pin 24 is slightly less than channel wall spacing 91. A further step in the installation process is rotating cassette 50 about mounting pin 24 into an installed position wherein catch surface 68 is engaged by retaining member 37. Tubing segment 74 may be opened for flow by manually sliding pinch occluder 84 to its non-occluding position described above.

The present invention is also embodied by a method of removing installed cassette 50 from peristaltic pump 12. The method comprises the steps of rotating the cassette about the mounting pin 24 until the truncated circumferential portion of the mounting pin is aligned with a juncture between the hinge journal 60 and the mounting channel 62 of the cassette, and moving the cassette 50 in a radial direction relative to mounting pin 24 such that the mounting pin passes from the hinge journal 60 into the mounting channel 62, and then out of the cassette via the mounting channel. In order to permit removal of cassette 50, tubing segment 74 may be closed for flow by manually sliding pinch occluder 84 to its occluding position, and catch surface 68 may be disengaged from retaining member 37 by operating eject button 100 as described above.

As may be appreciated, the present invention allows for easy installation and removal of a cassette without exposing the pumping mechanism portion of the pump. This improves safety by reducing the risk of inadvertently bumping or moving the cassette, and also provides a simplified pump design free of a movable door or movable cover over the pumping mechanism portion.

While the invention has been described in connection with exemplary embodiments, the detailed description is not intended to limit the scope of the invention to the particular forms set forth. The invention is intended to cover such alternatives, modifications and equivalents of the described embodiment as may be included within the spirit and scope of the invention.

LIST OF REFERENCE SIGNS

10 Pump assembly
12 Peristaltic pump
14 Pump body
16 Pumping mechanism portion
18 Inner wall of pumping mechanism portion
20 Outer wall of pumping mechanism portion
22 Slot opening of pumping mechanism portion
24 Cassette mounting pin of pumping mechanism portion
25 Shelf of pumping mechanism portion
26 Roller assembly
27 Rotational axis of roller assembly
28 Rotational drive shaft for roller assembly
29 Arc-shaped recess of shelf
30 Pinch rollers of roller assembly
31 Axle pins for individual pinch rollers
32 Upstream sensor
33 Downstream sensor
34 Swing arm supporting mounting pin and downstream sensor
35 Pivot pin for swing arm
36 Display on pump body
37 Retaining member of pumping mechanism portion
38 Keypad on pump body
39 Spring arranged to bias swing arm
50 Cassette
52 Cassette body
54 Rear wall of cassette body
56 Front wall of cassette body
58 Perimeter wall of cassette body
60 Hinge journal of cassette body
62 Mounting channel of cassette body
64 Race surface of cassette body
66 Upstream recess in cassette body
67 Downstream recess in cassette body
68 Closure catch surface of cassette body
70 Upstream end of cassette body
71 Downstream end of cassette body
72 View window in cassette body
74 Tubing segment
75A Outlet portion of tubing segment
75B Middle portion of tubing segment
75C Inlet portion of tubing segment
76 Direction of outlet portion of tubing segment
77 Tubing guides
78 Direction of mounting channel
79 Tubing connectors
80 Downstream supply tubing
82 Upstream supply tubing
84 Pinch occluder
85 Shaped passage of pinch occluder
86 Narrow region of shaped passage
87 Wide region of shaped passage
88 Slider button of pinch occluder
89 Enlarged end portion of pinch occluder
90A, 90B Opposed walls of mounting channel
91 Spacing between walls of mounting channel at hinge journal
92 Juncture of mounting channel with hinge journal
93 Inner diameter of hinge journal
94 Spacing between walls of mounting channel at channel mouth
95 Mouth of mounting channel
96 Flats on mounting pin
98 Non-truncated portions of mounting pin circumference
100 Eject button
102 Operation direction of eject button
104 Sliding direction of pinch occluder to its occluding position

What is claimed is:

1. A cassette for removable mounting on a peristaltic pump having a pump body and a mounting pin coupled to the pump body, the cassette comprising:
   a cassette body including rear wall, a front wall, a perimeter wall connecting the rear and front walls, and a hinge journal formed therein through the rear wall for slidably receiving the mounting pin of the peristaltic pump, wherein the cassette body is rotatable about an axis of the mounting pin relative to the pump body;
   the cassette body further including a mounting channel through the rear wall and the perimeter wall, the mounting channel communicating with the hinge journal;
   whereby the mounting pin is received into the hinge journal via the mounting channel by moving the cassette body in a radial direction relative to the mounting pin.

2. The cassette according to claim 1, further comprising a segment of tubing extending through the cassette body from an upstream end of the cassette body to a downstream end of the cassette body, the segment of tubing including an outlet portion near the downstream end of the cassette body, the outlet portion of the tubing segment extending in a first direction, wherein the mounting channel is an elongated channel extending in a second direction inclined relative to the first direction.

3. The cassette according to claim 1, wherein the mounting channel includes a pair of opposed channel walls and a spacing between the pair of channel walls at a juncture of the mounting channel with the hinge journal is less than an inner diameter of the hinge journal.

4. The cassette according to claim 3, wherein a spacing between the pair of channel walls at a location where the mounting channel opens through the perimeter wall is greater than the inner diameter of the hinge journal.

5. The cassette according to claim 4, wherein the pair of channel walls converge from the location where the mounting channel opens through the perimeter wall to the juncture of the mounting channel with the hinge journal.

6. The cassette according to claim 5, wherein the pair of channel walls converge linearly from the location where the mounting channel opens through the perimeter wall to the juncture of the mounting channel with the hinge journal.

7. The cassette according to claim 1, wherein the mounting channel is covered by the front wall of the cassette body.

8. A peristaltic pump assembly comprising:
   a peristaltic pump including a pumping mechanism portion having an inner wall and an outer wall opposing each other to define a slot opening therebetween, the pumping mechanism portion further having a cassette mounting pin extending at least partially across the slot opening; and
   a removable cassette including a cylindrical hinge journal and a mounting channel merging in a radial direction with the hinge journal, whereby the cassette is mounted on the mounting pin by inserting the removable cassette into the slot opening between the inner and outer walls of the pumping mechanism portion in a radial direction of the mounting pin such that the mounting pin is passed through the mounting channel and received by the hinge journal;
   wherein the mounting pin and hinge journal are configured to allow the removable cassette to rotate about the mounting pin into and out of a fully installed position.

9. The assembly according to claim 8, wherein the mounting channel includes a pair of opposed channel walls, and a spacing between the pair of channel walls at a juncture of the mounting channel with the hinge journal is less than a inner diameter of the hinge journal.

10. The assembly according to claim 9, wherein the mounting pin is a generally cylindrical mounting pin sized for slidable receipt by the hinge journal, and a circumference of the mounting pin is truncated to enable the pin to pass through the mounting channel and into the hinge journal.

11. The assembly according to claim 10, wherein the mounting pin and hinge journal are configured such that when the cassette is rotated into the fully installed position, the mounting pin is prevented from passing from the hinge journal into the mounting channel.

12. The assembly according to claim 11, wherein a spacing between the pair of channel walls at a location where the mounting channel opens through the perimeter wall is greater than the diameter of the mounting pin.

13. The assembly according to claim 12, wherein the pair of channel walls converge from the location where the mounting channel opens through the perimeter wall to the juncture of the mounting channel with the hinge journal.

14. The assembly according to claim 13, wherein the pair of channel walls converge linearly from the location where the mounting channel opens through the perimeter wall to the juncture of the mounting channel with the hinge journal.

15. The assembly according to claim 8, wherein the cassette includes a cassette body having a rear wall, a front wall, and a perimeter wall connecting the rear and front walls, wherein the mounting channel is covered by the front wall of the cassette body.

16. The assembly according to claim 8, wherein the cassette further includes a segment of tubing for conveying fluid through the cassette, and the pumping mechanism portion further has:
   a swing arm mounted to the inner wall to pivot about an axis, the mounting pin being supported by the swing arm at a location spaced from the pivot axis of the swing arm;
   a roller assembly comprising a plurality of pinch rollers, the roller assembly having an axis of rotation parallel to the pivot axis of the swing arm; and
   a spring arranged to resiliently bias the swing arm about the pivot axis of the swing arm such that the segment of tubing of the cassette is resiliently biased toward contact with at least one of the plurality of pinch rollers.

17. The assembly according to claim 16, further comprising a sensor supported by the swing arm.

18. The assembly according to claim 17, wherein the sensor is arranged on the swing arm adjacent the mounting pin.

19. A method of installing a removable cassette on a peristaltic pump, the peristaltic pump including a generally cylindrical mounting pin, the method comprising the steps of:
   aligning the cassette relative to the mounting pin such that a mouth of a mounting channel of the cassette is radially adjacent the mounting pin;
   moving the cassette in a radial direction relative to the mounting pin such that the mounting pin passes through the mounting channel and into a hinge journal of the cassette; and
   rotating the cassette about the mounting pin into an installed position.

20. A method of removing a removable cassette from a peristaltic pump, the peristaltic pump including a generally cylindrical mounting pin received by a cylindrical hinge journal of the cassette, the method comprising the steps of:
   rotating the cassette about the mounting pin until a truncated circumferential portion of the mounting pin is aligned with a juncture between the hinge journal and a mounting channel of the cassette;

moving the cassette in a radial direction relative to the mounting pin such that the mounting pin passes from the hinge journal into the mounting channel and out of the cassette via the mounting channel.

\* \* \* \* \*